United States Patent [19]
Pomfrett

[11] Patent Number: 5,372,140
[45] Date of Patent: Dec. 13, 1994

[54] DEPTH OF ANAESTHESIA MONITORING

[75] Inventor: Christopher J. D. Pomfrett, Sandbach, United Kingdom

[73] Assignee: The Victoria University of Manchester, Manchester, England

[21] Appl. No.: 39,122

[22] PCT Filed: Oct. 16, 1991

[86] PCT No.: PCT/GB91/01807
§ 371 Date: Feb. 13, 1993
§ 102(e) Date: Feb. 13, 1993

[87] PCT Pub. No.: WO92/06632
PCT Pub. Date: Apr. 30, 1992

[30] Foreign Application Priority Data
Oct. 18, 1990 [GB] United Kingdom ............... 9022623

[51] Int. Cl.$^5$ .......................................... A61B 5/0456
[52] U.S. Cl. ................................... 128/700; 128/671
[58] Field of Search ............... 128/700, 670, 706, 708, 128/671

[56] References Cited
U.S. PATENT DOCUMENTS

| | | | |
|---|---|---|---|
| 3,946,725 | 3/1976 | Bolshov et al. | 128/706 |
| 4,519,395 | 5/1985 | Hrusheskey | 128/671 |
| 4,788,982 | 12/1988 | Gedeon et al. | 128/670 |

Primary Examiner—William E. Kamm
Assistant Examiner—Kennedy J. Schaetzle
Attorney, Agent, or Firm—Nixon & Vanderhye

[57] ABSTRACT

A method and apparatus for providing a measure of the depth of anaesthesia. A series of R-waves are analyzed using circular statistics to derive a measurement vector length representing the R—R variation of the sample. The Rayleigh Test is applied to determine a reference vector length from a predetermined probability level and the number of R-waves in the analyzed series. The measurement vector length is compared to the reference vector length to derive a measure of the death of anaesthesia.

10 Claims, 8 Drawing Sheets

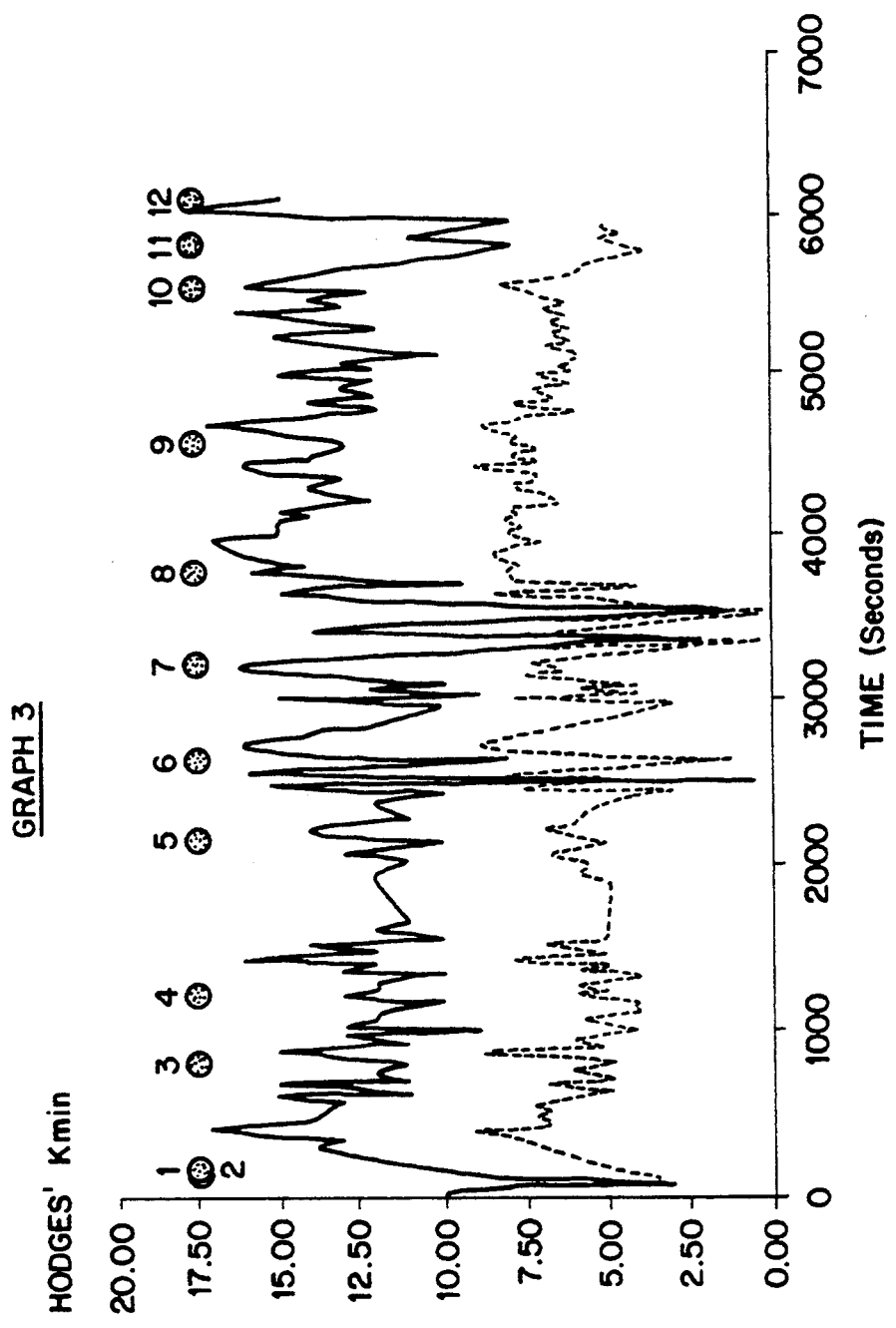

DEPTH OF ANAESTHESIA MONITORING

BACKGROUND OF THE INVENTION

1. Field of the Invention

The present invention relates to an apparatus and method for monitoring the depth of anaesthesia.

2. Related Art

Monitoring the depth of anaesthesia is a well-known objective as indicated by the pamphlet "Anaesthesia Rounds" No. 21 issued by ICI Pharmaceuticals, Alderley Park, Macclesfield, Cheshire, England in 1988. This publication summarises various techniques which have been proposed for monitoring the depth of anaesthesia. Interest in this subject has increased in recent years as the result of growing evidence that in a small but not negligible number of cases, patients are aware of their surroundings during anaesthesia. It is probable that the problem of awareness under anaesthesia has increased due to the availability of anaesthetics from which recovery is relatively rapid. The above publication outlines a wide range of possible methods of monitoring depth of anaesthesia which are considered to merit further study. These include electroencephalogram (EEG) analysis, auditory evoked responses (AER), autonomic signs, surface electromyogram (EMG), and oesophageal contractility.

The investigation of the depth of anaesthesia by using the various techniques mentioned above has enabled a body of data to be assembled which can indicate to anaesthetists appropriate anaesthetic techniques whereby different categories of patient can be anaesthetized reliably in most circumstances. This body of data is not sufficient, however, to cover all the circumstances and it is therefore necessary for the anaesthetist to maintain a very close watch on a patient during, for example, a surgical procedure. Given that modern anaesthetics have recovery periods of only two or three minutes in some circumstances, it is necessary for the anaesthetist to very closely monitor a patient almost continuously. Ideally a system should be provided which can give a real time indication of the depth of anaesthesia, but no such system has been made available.

The article "An Improved Method of Measuring Heart-rate Variability: Assessment of Cardiac Autonomic Function", Biometrics 40,855-861, September 1984 by C. R. Weinberg and M. A. Pfeifer, describes various techniques for assessing sinus arrhythmia using the R—R interval, that is the interval between the easily-distinguished spikes in an electrocardiogram (ECG). This parameter is used, for example, to distinguish between diabetics and others. The article notes that problems arise in relying simply on the R—R interval. For example, the standard deviation of the R—R interval varies with respiratory rate. It is suggested that the patient should maintain a fixed frequency of respiration. A new measure of sinus arrhythmia is suggested, based on the application of circular statistics, but it appears that a fixed rated of respiration is still required. There is no suggestion that the derived information could be used in real time to monitor the depth of anaesthesia, the technique being put forward essentially with the purpose of enabling better identification of diabetics.

In the article "Respiratory Sinus Arrhythmia During Recovery From Isoflurane-nitrous-oxide Anaesthesia), Anesth. Analg. 1985; 64:811-15, by Y. Donchin, J. M. Feld, and S. W. Porges, it is suggested that on-line analysis of respiratory sinus arrhythmia, provides a physiological index of the depth of anaesthesia and the rate of recovery from anaesthesia. The measure proposes monitoring the variance of the heart rate pattern in the frequency band of respirations, this measure being indicative of the depth of anaesthesia. An arbitrary limit is suggested against which this measure is compared to determine the depth of anaesthesia and thus the reference limit is not patient specific. As it is not patient specific, it is unlikely that anaesthetists could rely upon this method to give real time indications of a need to increase the supply of anaesthetic to a patient to prevent premature recovery. This is because different patient exhibit different sinus arrhythmia responses, when anaesthetized. For example, in the extreme case of diabetics no response is detectable.

In the article "RR Variation: The Autonomic Test of Choice in Diabetes". Diabetes/Metabolism Reviews, Vol. 4, No. 3, 255-271 (1988), by H. Genovely and N. A. Pfeifer, further work related to the use of sinus arrhythmia in the diagnosis of diabetics is described. This article elaborates the application of circular statistics to derive a measure of sinus arrhythmia. It is also suggested that the periodicity of the unit circle used in the circular statistical analysis may be changed to match variations in respiratory rate in, for example, children and animals where the "patient" cannot be relied upon to co-operate by breathing at a regular rate. It describes the significance of "clustering" in circular statistics, the degree of clustering being identified by the length of a vector. The greater the length of the vector, the larger is the R—R variation and hence the sinus arrhythmia. Thus techniques are known which enable a measure of sinus arrhythmia to be derived but not to correlate measurements of sinus arrhythmia with the depth of anaesthesia or the rate of recovery of a specific patient.

SUMMARY OF THE INVENTION

It is an object of the present invention to provide a system which enables a measurement of sinus arrhythmia to provide a real time indication of the depth of anaesthesia.

According to the present invention, there is provided a method for providing a measure of the depth of anaesthesia, wherein a series of R-waves is analyzed to determine the position in time of each R-wave relative to the respiratory cycle within which it occurs, a measurement value is derived representing the degree of clustering of the analyzed R-waves relative to the respiratory cycles, a test for randomness is applied to the analyzed series of R-waves to derive a reference value representing a predetermined significance level for clustering of the R-waves relative to the respiratory cycles, and the measurement value is compared with the reference value to derive a measure of the depth of anaesthesia. Preferably, the position in time of the R-waves on a normalised unit of respiratory waveform is determined, each R-wave is resolved as a vector with a unit amplitude and an angle representing the portion of the R-wave in the respiratory cycle, and the resultant mean vector length is calculated to form said measurement value. The test for randomness is applied to determine a reference vector length to form said reference value, the reference vector length corresponding to a predetermined probability level and the number of R-waves in the said series. Preferably, the Rayleigh test is applied to determine the degree of randomness.

The Rayleigh Test is described in Chapter 4 of "Circular Statistics in Biology", Batschelet E. (1981), Academic Press (Mathematics in Biology. Series Eds Sibson R. and Cohen J. E.), ISBN 0-12-081050-6. The Rayleigh Test in essence provides a test for randomness and goodness-of-fit. Alternative tests are however available to test for randomness, some of the alternative tests also being described by Batschelet. For example, the Rao test or the Hodges and Ajne tests may be used in accordance with the present invention.

Preferably the reference vector length is obtained by reference to a table correlating the number of R-waves in the sample to the length of the vector that will result given that number of R-waves for a given probability. A probability level of, for example, ninety-five per cent can be used to correlate the number of R-waves in a sample to the length of the reference vector. It may be, however, that after sufficient clinical trials have been conducted a different reference probability level will be considered more appropriate. Particularly in the case of older patients, it appears that a lower probability reference level, for example, ninety per cent, would be appropriate. The analysis of the series of R-waves using circular statistics requires a knowledge of the rate of respiration of the patient. This could be achieved by controlling the respiratory rate, but preferably means will be provided for directly monitoring the respiratory rate and incorporating this data in the data to be analysed. Essentially this involves adjusting the periodicity of the unit circle used in the circular statistical analysis to match variations in the respiratory rate. This can be achieved readily easily by incorporating a breathing monitor in the equipment used to deliver anaesthetic to the patient.

Preferably the measurement vector length and reference vector length are displayed simultaneously to provide the anaesthetist with a real time indication of the depth of anaesthesia. Both the measurement vector length and the reference vector length are dynamic and therefore trends in the variation of both parameters can be readily displayed. For example, it is preferred to display the measurement and vector length graphically using a bar-chart in which the two parameters are illustrated by adjacent bars of different colours. Tests have shown that given a reference probability level of ninety-five per cent, the measurement vector length is in nearly all cases less than the reference vector length. This rule does not apply occasionally, dependent upon particular patient responses to, for example, surgical incisions or other procedures, but it is unusual for the measurement vector length to be shorter than the reference vector length and very unusual indeed for the reference vector length to be shorter than the measurement vector length for two consecutive samples. Thus the present invention gives a high degree of reliability and serves as a very good indicator to an anaesthetist of the depth of anaesthesia of a patient. There are, of course, some patients who do not display the sinus arrhythmia which is central to the present invention. As will be appreciated from the above papers, patients suffering from diabetes are one group for whom the present invention cannot provide much useful information. Such groups can, however, be screened by using a control period prior to the induction of anaesthesia to determine the relative vector lengths. If a patient does not exhibit sinus arrhythmia the anaesthetist will know that the present invention is not applicable to that patient.

The present invention also provides an apparatus for providing a measure of the depth of anaesthesia, comprising means for analyzing a series of R-waves to determine the position in time of each R-wave relative to the respiratory cycle within which it occurs, means for deriving a measurement value representing the degree of clustering of the analyzed R-waves relative to the respiratory cycles, means for applying a test for randomness to the analyzed series of R-waves to derive a reference value representing a predetermined significance level for clustering of the R-waves relative to the respiratory cycle, and means for comparing the measurement value with the reference value to derive a measure of depth of anaesthesia.

It will be appreciated that the present invention can be applied to most patients in a routine manner. It will also be appreciated that the invention will have applications in veterinary practice as it is in no way dependent upon information derived from the "patient" to give an indication of the depth of anaesthesia.

BRIEF DESCRIPTION OF THE DRAWINGS

An embodiment of the present invention will now be described, by way of example, with reference to the accompanying drawings, in which.

Figure 7:
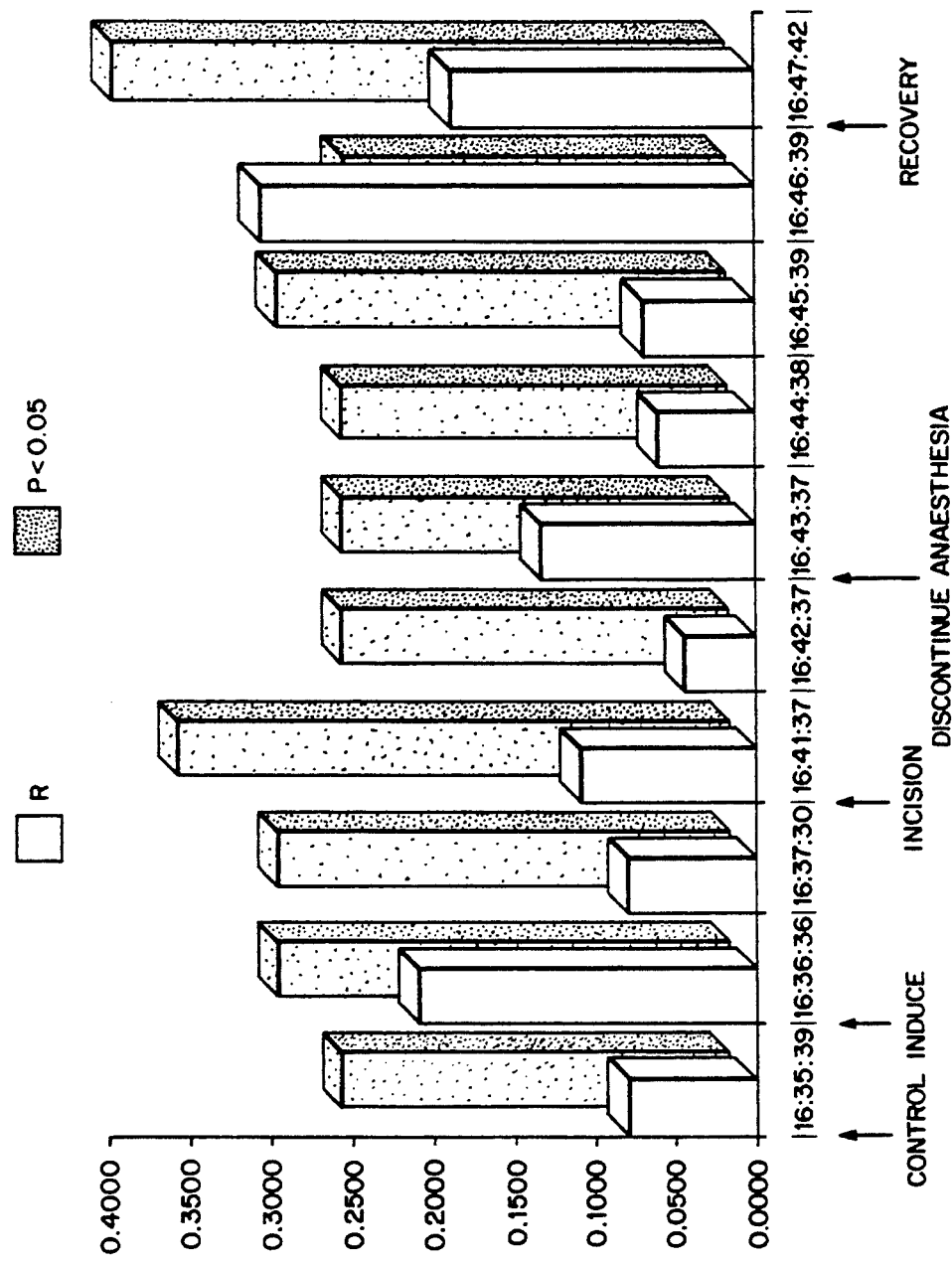
Figure 8:
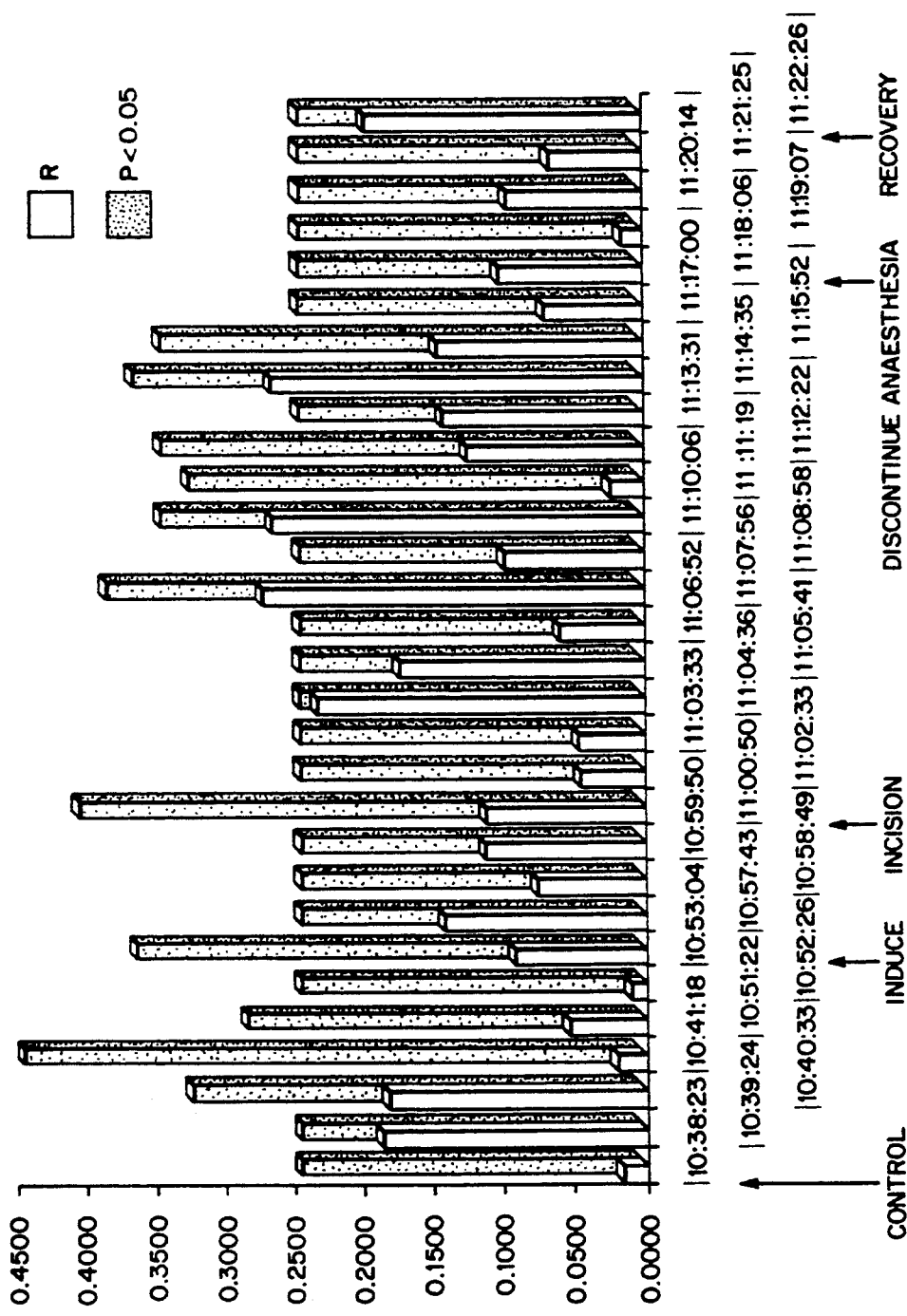
Figure 9A:
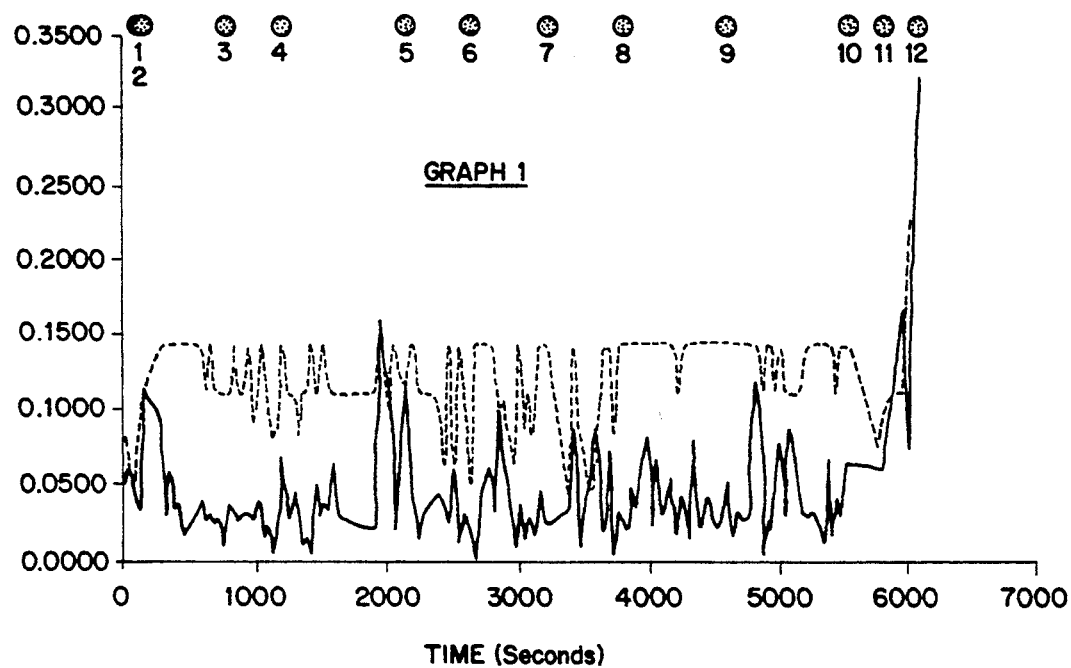
Figure 9B:
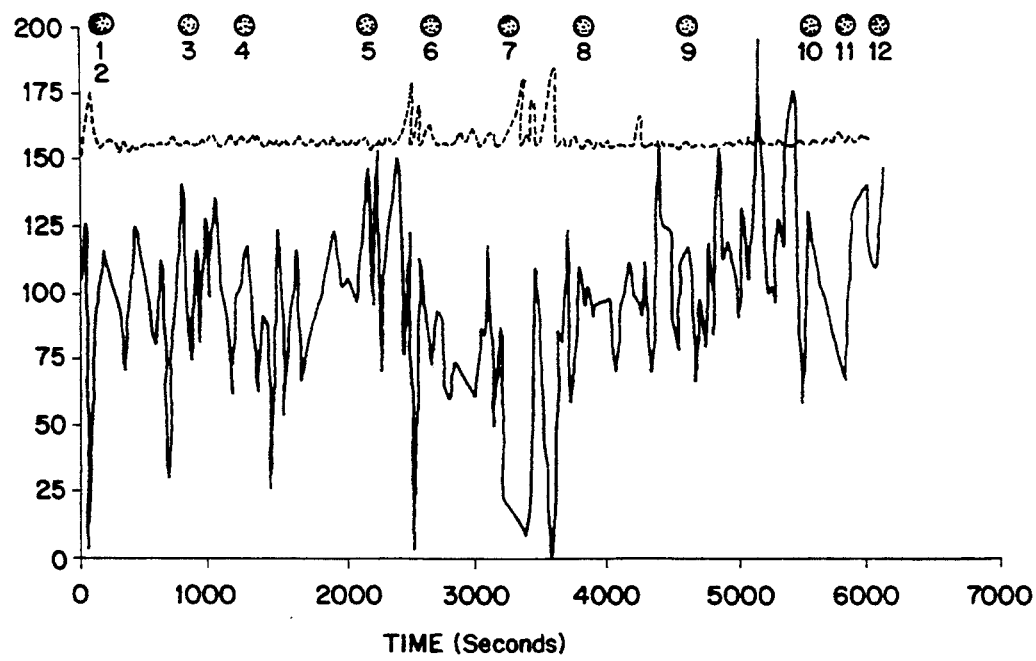

FIG., 6 is a schematic illustration of the operation of software intended to implement an embodiment of the present invention;

FIG. 7 illustrates the display resulting from the application of the invention to a female patient having an age of thirty-six years;

FIG. 8 illustrates the display resulting from the application of the invention to a male patient of eighty-seven years; and FIGS. 9A–9C illustrates results achieved using different statistical approaches to the analysis of R-waves in accordance with the invention.

DETAILED DESCRIPTION OF THE PREFERRED EMBODIMENTS

Figure 1:
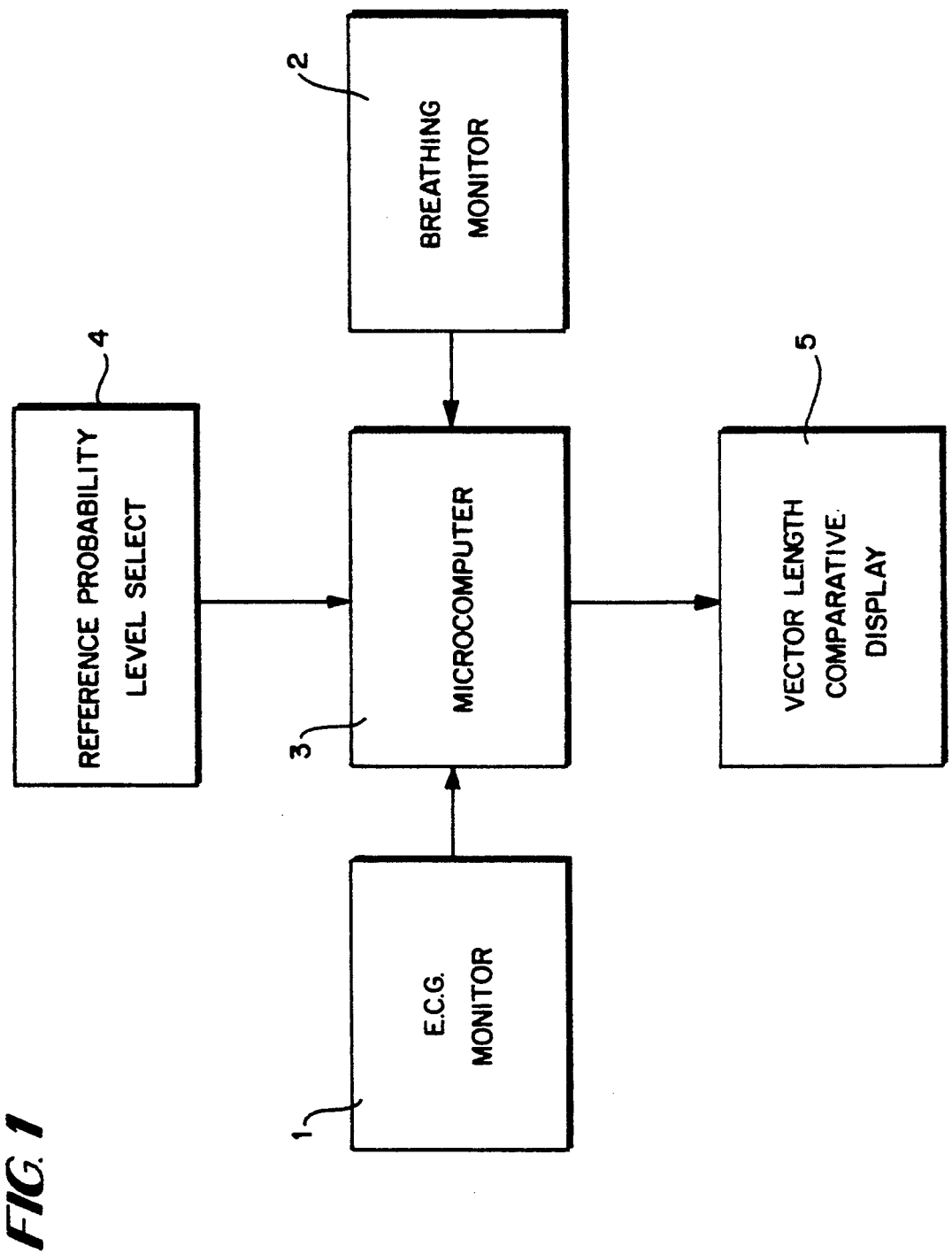
FIG. 1 is a schematic illustration of the functional component of an embodiment of the invention.

Referring to FIG. 1, this illustrates the basic components of the system in accordance with the present invention. An ECG Monitor 1 and a Breathing Monitor 2 supply to a Microcomputer 3 basic data related to a subject patient's condition. The anaesthetist also inputs a reference probability level appropriate to that patient via an Input Unit 4. The Microcomputer then calculates a measurement vector length and a reference vector length and outputs these to a vector length comparative display 5. Generally the comparative display 5 would include a graphical representation of the relative lengths of the two vectors, but it would be possible for the two vector lengths simply to be displayed as appropriate numbers.

The microcomputer 3 stores and analyses physiological data in real time as it is collected from patients undergoing routine surgery. The display is presented to the anaesthetist who may then use the displayed information as an adjunct to his repertoire of existing techniques to ensure adequate anaesthesia.

The electrocardiogram (ECG) is obtained using conventional recording techniques, e.g. Digitimer Neurolog AC amplifiers and filters, to give an analogue waveform in the range +5 V peak to peak. A Schmidt trigger is used to pick off the R-wave from the ECG, and this gives a one TTL pulse for each ECG R-wave. The quality or the ECG is monitored using a conventional oscilloscope. The respiratory cycle is encoded using a flow meter introduced into the anaesthetic circuit, e.g. a Magtrak flow sensor. This sensor gives a stream of TTL pulses with each inspiration. The analogue ECG waveform is digitized to 12-bit and 1 ms accuracy using a fast ADC convertor incorporated in a laboratory interface, e.g. Cambridge Electronic Design 1401. The interface also encodes the TTL R-wave and respiratory pulses as events to 1 ms accuracy using onboard software. The digitized and event data are then transferred under software control to the microcomputer via. a 1 MHz data bus. The microcomputer is an Acorn Archimedes A410/1 32 bit RISC workstation fitted with RISC OS 2.00 ROMS, 4 MBytes of RAM and an ARM3 CPU running at 20 MHZ. Raw and worked data are saved to a 50 MByte Winchester Hard Disc without interrupting data acquisition and further archiving is to a 60 MByte SCSI tapestreamer.

Figure 2:
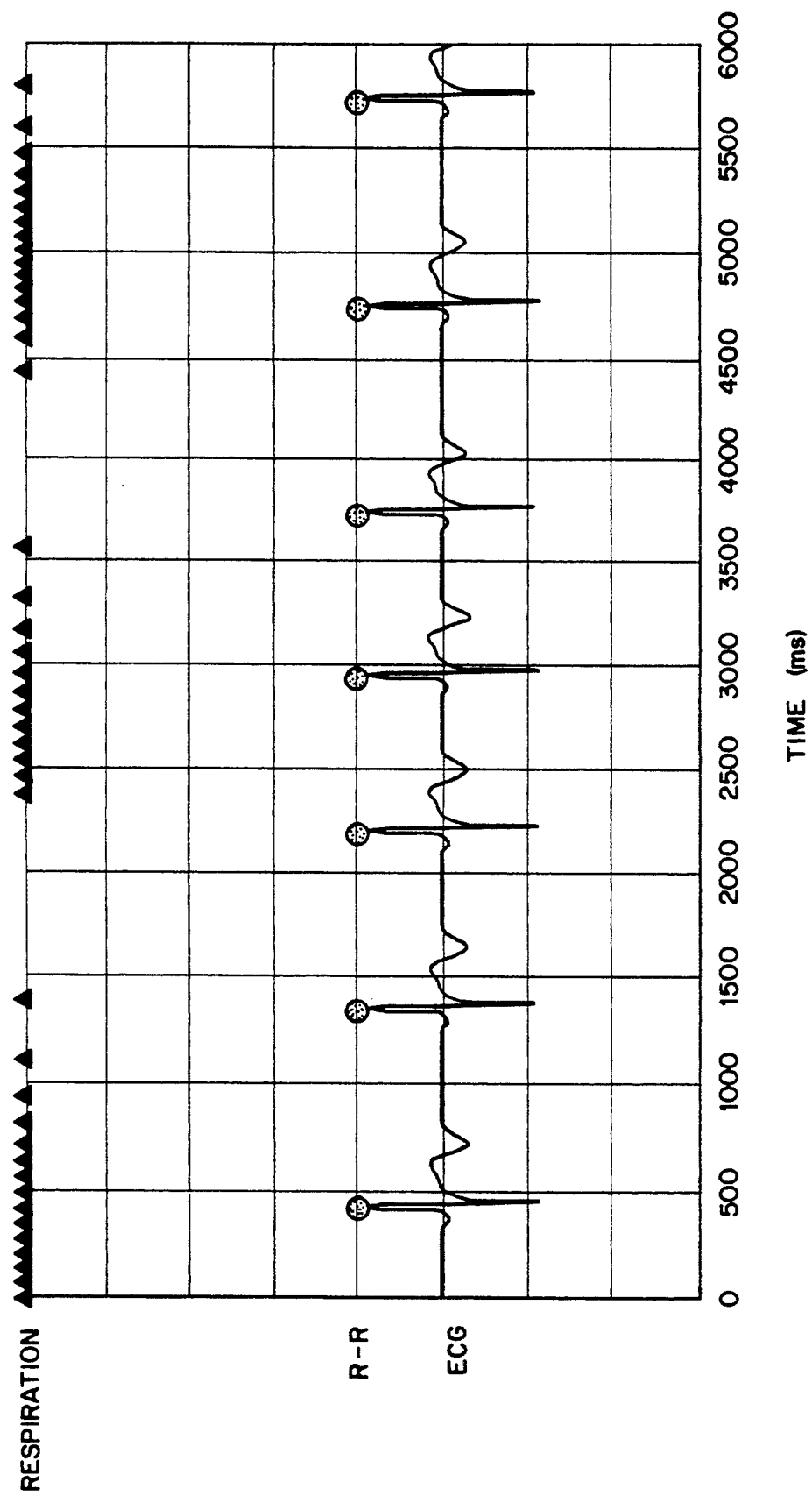
FIG. 2 illustrates an ECG and an associated respiratory cycle.

The interface gathers the ECG data and the respiration data and uses double buffering so that, at six second intervals, raw data is transferred to the microcomputer without interrupting data acquisitions. Data acquisition is started by a simple input generated by the anaesthetist. FIG. 2 illustrates an ECG obtained from a patient and associated respiration and R—R data. This data is used to provide the appropriate depth of anaesthesia indication. The data is converted into the form graphically represented in FIG. 3, that is a series of respiratory cycles each initiated a short time after a patient starts to draw breath in, and the R-wave locations relative to those respiratory cycles.

Figure 3:
FIG. 3 schematically represents the respiratory cycles of FIG. 2 with the associated R-wave locations.
Figure 4:
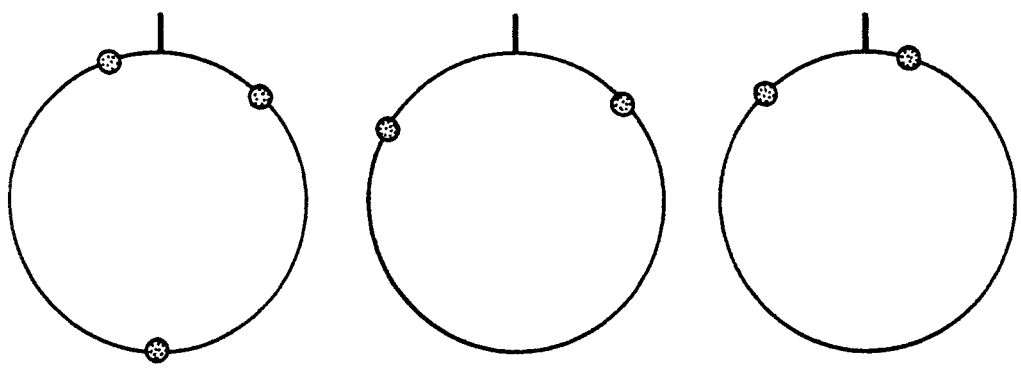
FIG. 4 represents normalized unit circles based on the respiratory cycles illustrated in FIGS. 2 & 3.
Figure 5:
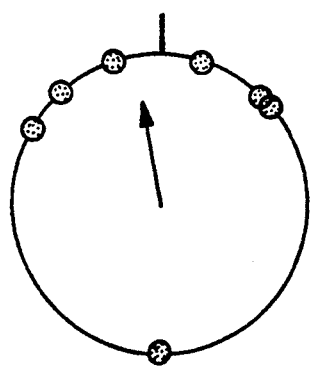
FIG. 5 illustrates the result of combining the unit circles of FIG. 4.

The data represented in FIG. 3 is then converted into normalized unit circles based upon the respiratory cycles. Thus the diameters of all the circles are the same even though the respective respiratory cycles are not of the same duration. The data represented in FIG. 4 is then combined on a single unit circle with the R-wave locations of all the respiratory cycles superimposed on that single circle. An arrow in FIG. 5 represents the mean vector angle and the mean vector length. The greater the length of the vector, the greater is the degree of clustering and hence the level of sinus arrhythmia. Thus the length of the arrow in FIG. 5 represents a measure of the sinus arrhythmia.

Figure 6:
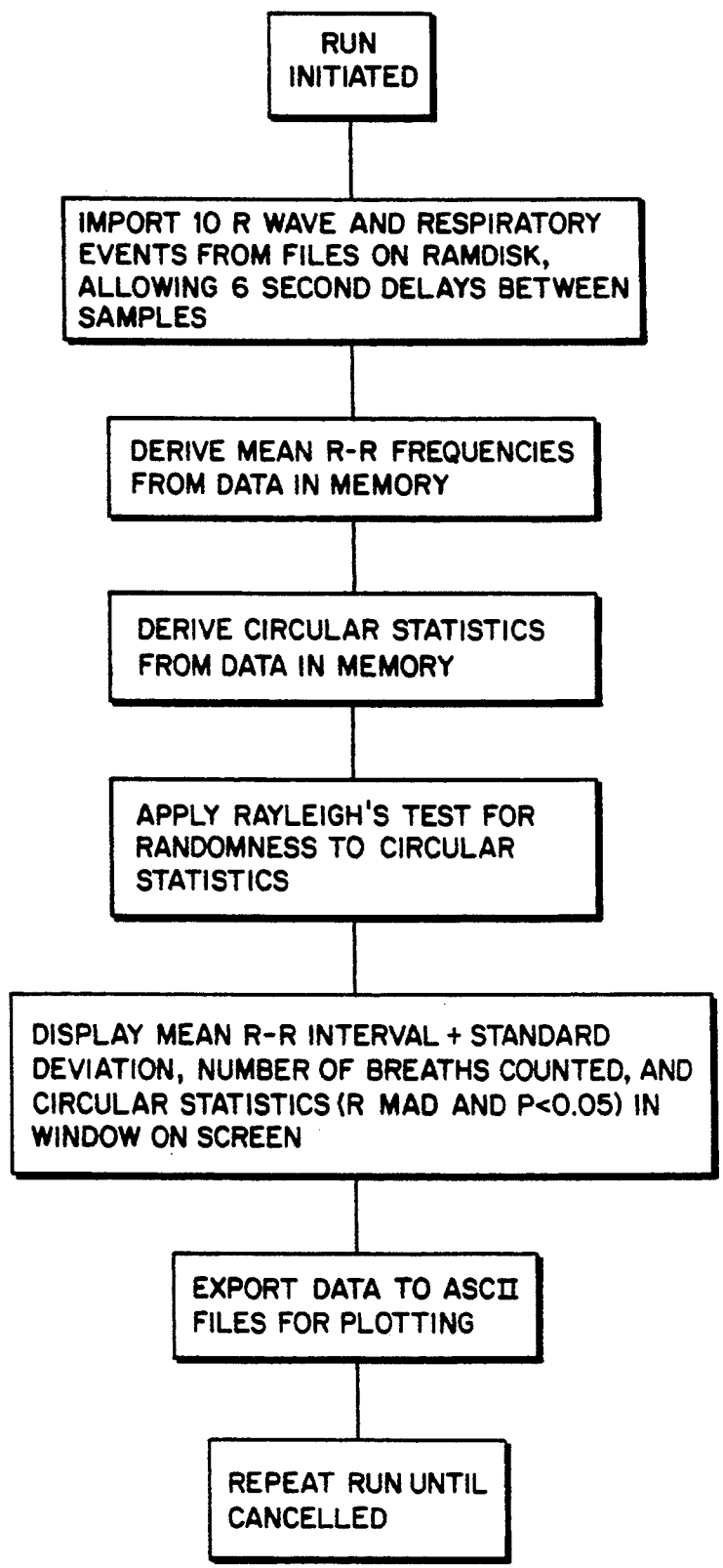

Referring to FIG. 6, this illustrates the operation of the system. After a run is initiated, ten R-wave and respiratory events are imported from files on a random access disc, allowing six second delays between the samples. This data is used to derive mean R—R frequencies and to derive circular statistics. Rayleigh's test for randomness is then applied to the circular statistics. The mean R—R interval, standard deviation, number of breaths and circular statistics are then displayed in a window or an appropriate display screen. In addition the relative measurement and reference vector length are displayed graphically by an appropriate plotting device and the system continues to operate until the run is cancelled.

FIG. 7 illustrates the graphical display produced in the case of a 36 year old female patient. The vertical axis represents vector length and the horizontal axis time. It can seen that fresh information is displayed at approximately 1 minute intervals. The lightly shaded columns represent the lengths of the calculated measurement vectors. The darker columns represent the length of the calculated reference vectors. With the exception of the ninth sample the reference length is also always substantially greater than the measurement vector length. A control period is initiated at time 16:35:39. Anaesthetic is induced at time 16:36:36. An incision is made at time 16:41:37 (it being noted that no data is displayed for a four minute period upto the incision). The anaesthesia is discontinued at time 16:43:37 and the patient recovers at time 16:47:42. At all time during the surgical procedure the anaesthetist can be confident that the relative lengths of the columns indicates an acceptable depth of anaesthesia. The columns indicated at time period 16:46:39 indicate that the patient is recovering from anaesthesia. As this results from the deliberate discontinuation of anaesthesia the anaesthetist would not be concerned. If however similar relative column lengths occurred for example at time 16:43:37 the anaesthetist would be alerted to a problem having arisen and would therefore be prompted to determine whether or not further action was necessary to prevent premature recovery.

FIG. 8 illustrates the graphical display resulting from the application of the present invention in the case of an 87 year old male. As in the case of FIG. 7, a reference probability level of 95% has been used to generate the information represented by the darker shaded columns. This is indicated by P being less than 0.05. The information displayed in FIG. 8 indicates a probability that the patient has some age-induced neuropathy, leading to variable sinus arrhythmia and the potential for a misleading result. Nevertheless even with this patient at no time does the measurement vector length exceed the reference vector length. Although the measurement vector length does vary somewhat erratically. The anaesthetist might be caused concern at time 11:04:36 but that concern would be reduced at time 11:05:41. Even with a patient giving an unusual response of this type therefore the information provided by the present invention a useful addition to the information which the anaesthetist has to consider when monitoring any procedure. The more typical response indicated by FIG. 7 shows a rise in sinus arrhythmia associated with light anaesthesia at the beginning of the procedure (induction) and a significant rise before recovery. Such a significant rise in a patient paralysed with muscle relaxants during surgery would definitely prompt the anaesthetist to look for some inadequacy of anaesthetic.

Referring now to FIG. 9A–9C graphs 1, 2 and 3 of these Figures all relate to a single anaesthetic procedure carried out on a female patient fifty three years of age. The patient was anaesthetized initially with intravenous propofol and subsequently maintained with isoflurane in nitrous oxide/oxygen. The operation was to perform a biopsy of suspect breast tissue.

Graphs 1 to 3 show comparisons of the changing statistics over the same time interval. Events are indicated as numbered spots: 1) Propofol Anaesthesia; 2) Intubate; 3) 1.7% Isoflurane; 4) 0.85% Isoflurane; 5) Incision; 6) 1.7% Isoflurane; 7) 0.85% Isoflurane; 8) 1.7% Isoflurane; 9) 0.85% Isoflurane; 10) Isoflurane discontinued; 11) Patient coughing; 12) Patient responding to verbal commands.

Graph 1 shows Rayleigh test statistics with the mean vector length angle (R) as the solid line and the dotted line as the P<0.05 level for the Rayleigh test, significance being assigned if R is greater than the P level. Graph 2 shows the results of the Rao spacing test with the solid line as the test statistic U and the dotted line as the P<0.05 critical level, significance being assigned if U is greater than the P level. Graph 3 shows the results of the Hodges' and Ajne's test. In this test, the test statistic K is shown as the solid line and the P<0.05 level is the dotted line, and significance is assigned if K is less than the P level.

Thus it can be seen that with all three statistical tests, that is Rayleigh, Raos and Hodges and Ajne, a useful indication of the depth of anaesthesia is obtained. It is apparent that at least for the subject patient the Rayleigh test is best at detecting sinus arrhythmia and lightening of anaesthesia. The Rao spacing test is however sensitive to subtle changes in anaesthesia depth. The Hodges and Ajne test was the least sensitive of the three in this application. Of course, it would be possible to display the results of more than one test simultaneously to enable the anaesthetist to monitor discrepancies between different tests.

I claim:

1. A method for providing a measure of the depth of anaesthesia, said method comprising the steps of:
    analyzing a series of R-waves to determine the position in time of each R-wave relative to the respiratory cycle within which it occurs,
    deriving a measurement value representing the degree of clustering of the analyzed R-waves relative to the respiratory cycles,
    applying a test for randomness to the analyzed series of R-waves to derive a reference value representing a predetermined significance level for clustering of the R-waves relative to the respiratory cycles, and
    comparing the measurement value with the reference value to derive a measure of the depth of anaesthesia.

2. A method according to claim 1, including:
    determining the position in time of the R-waves on a normalised unit of respiratory waveform,
    resolving each R-wave as a vector with a unit amplitude and an angle representing the portion of the R-wave in the respiratory cycle, and
    calculating the resultant mean vector length to form said measurement value.

3. A method according to claim 2, including:
    applying the test for randomness to determine a reference vector length to form said reference value, the reference vector length corresponding to a predetermined probability level and the number of R-waves in the said series.

4. A method according to claim 3, wherein the test for randomness is the Rayleigh test.

5. A method according to claim 4, including obtaining the reference vector length by reference to a table correlating the number of R-waves in the sample to the length of the vector that will result given that number of R-waves for a given probability.

6. A method according to claim 5, wherein the given probability is 95%.

7. A method according to claim 1, including monitoring the respiratory rate.

8. A method according to claim 1, including displaying the measurement vector length and reference vector length simultaneously to provide the anaesthetist with a real time indication of the depth of anaesthesia.

9. A method according to claim 8, including displaying the measurement and vector lengths graphically using a bar-chart in which the two parameters are illustrated by adjacent bars of different colours.

10. An apparatus for providing a measure of the depth of anaesthesia, comprising:
    means for analyzing a series of R-waves to determine the position in time of each R-wave relative to the respiratory cycle within which it occurs,
    means for achieving a measurement value representing the degree of clustering of the analyzed R-waves relative to the respiratory cycles,
    means for applying a test for randomness to the analyzed series of R-waves to derive a reference value representing a predetermined significance level for clustering of the R-waves relative to the respiratory cycle, and
    means for comparing the measurement value with the reference value to derive a measurement of depth of anaesthesia.

* * * * *